(12) United States Patent
Mayer

(10) Patent No.: US 10,335,219 B2
(45) Date of Patent: Jul. 2, 2019

(54) METHOD AND IMPLANT FOR STABILIZING TWO BONE PORTIONS SEPARATED BY A CUT OR FRACTURE

(71) Applicant: Woodwelding AG, Stansstad (CH)

(72) Inventor: Jörg Mayer, Niederlenz (CH)

(73) Assignee: WOODWELDING AG, Stansstad (CH)

( * ) Notice: Subject to any disclaimer, the term of this patent is extended or adjusted under 35 U.S.C. 154(b) by 263 days.

(21) Appl. No.: 15/402,484

(22) Filed: Jan. 10, 2017

(65) Prior Publication Data
US 2017/0172637 A1    Jun. 22, 2017

Related U.S. Application Data

(62) Division of application No. 13/876,331, filed as application No. PCT/CH2011/000207 on Sep. 6, 2011, now Pat. No. 9,566,103.
(Continued)

(51) Int. Cl.
*A61B 17/88* (2006.01)
*A61B 17/064* (2006.01)
(Continued)

(52) U.S. Cl.
CPC ...... *A61B 17/8866* (2013.01); *A61B 17/0642* (2013.01); *A61B 17/17* (2013.01); *A61B 17/8872* (2013.01); *A61B 17/15* (2013.01); *A61B 2017/00831* (2013.01); *A61B 2017/00955* (2013.01); *A61B 2017/90* (2013.01)

(58) Field of Classification Search
CPC .. A61B 2017/00955; A61B 2017/0619; A61B 17/064; A61B 17/0642; A61B 17/0645
See application file for complete search history.

(56) References Cited

U.S. PATENT DOCUMENTS 3,960,147 A    6/1976    Murray
5,053,038 A    10/1991   Sheehan
(Continued)

FOREIGN PATENT DOCUMENTS

JP         2007-503292      2/2007
WO    WO 2007092869 A2 *  8/2007    ......... A61B 17/0401
(Continued)

*Primary Examiner* — Anu Ramana
(74) *Attorney, Agent, or Firm* — Rankin, Hill & Clark LLP

(57) ABSTRACT

In a human or animal patient, two bone portions separated by a cut or fracture are stabilized in a desired position relative to each other by bringing the two bone portions into this desired position, by pulling them against each other, by providing an opening having a mouth on a bone surface and reaching across the cut or fracture and walls in both bone portions, by inserting an implant into the opening and anchoring the implant in the walls of the opening with the aid of a material having thermoplastic properties and energy transmitted into the implant for in situ liquefaction of at least part of the material having thermoplastic properties. One exemplary application of the stabilizing procedure concerns the two tibial bone portions separated by tibial plateau leveling osteotomy in a canine patient suffering from cranial cruciate ligament damage or rupture in a stifle joint.

3 Claims, 10 Drawing Sheets

Related U.S. Application Data

(60) Provisional application No. 61/388,246, filed on Sep. 30, 2010.

(51) Int. Cl.
    *A61B 17/17*     (2006.01)
    *A61B 17/15*     (2006.01)
    *A61B 17/00*     (2006.01)
    *A61B 17/90*     (2006.01)

(56) References Cited

U.S. PATENT DOCUMENTS

| | | | |
|---|---|---|---|
| 5,502,158 A * | 3/1996 | Sinclair | A61L 15/26 528/354 |
| 7,008,226 B2 | 3/2006 | Mayer et al. | |
| 7,144,414 B2 | 12/2006 | Harvie et al. | |
| 7,335,205 B2 | 2/2008 | Aeschlimann et al. | |
| 8,951,254 B2 | 2/2015 | Mayer et al. | |
| 2004/0030341 A1 | 2/2004 | Aeschlimann et al. | |
| 2006/0105295 A1 | 5/2006 | Mayer et al. | |
| 2007/0088437 A1 | 4/2007 | Betz et al. | |
| 2008/0109007 A1 | 5/2008 | Schwager et al. | |
| 2008/0109080 A1 | 5/2008 | Aeschlimann et al. | |
| 2008/0262517 A1 | 10/2008 | Wieland | |
| 2008/0269649 A1 | 10/2008 | Dorawa | |
| 2009/0131947 A1 | 5/2009 | Aeschlimann et al. | |
| 2010/0049179 A1 | 2/2010 | Kanaoka et al. | |

FOREIGN PATENT DOCUMENTS

| | | |
|---|---|---|
| WO | 2008/034276 | 3/2008 |
| WO | 2009/109057 | 9/2009 |
| WO | 2009/132472 | 11/2009 |
| WO | 2010/045749 | 4/2010 |
| WO | 2010/085538 | 7/2010 |
| WO | 2010/096942 | 9/2010 |

* cited by examiner

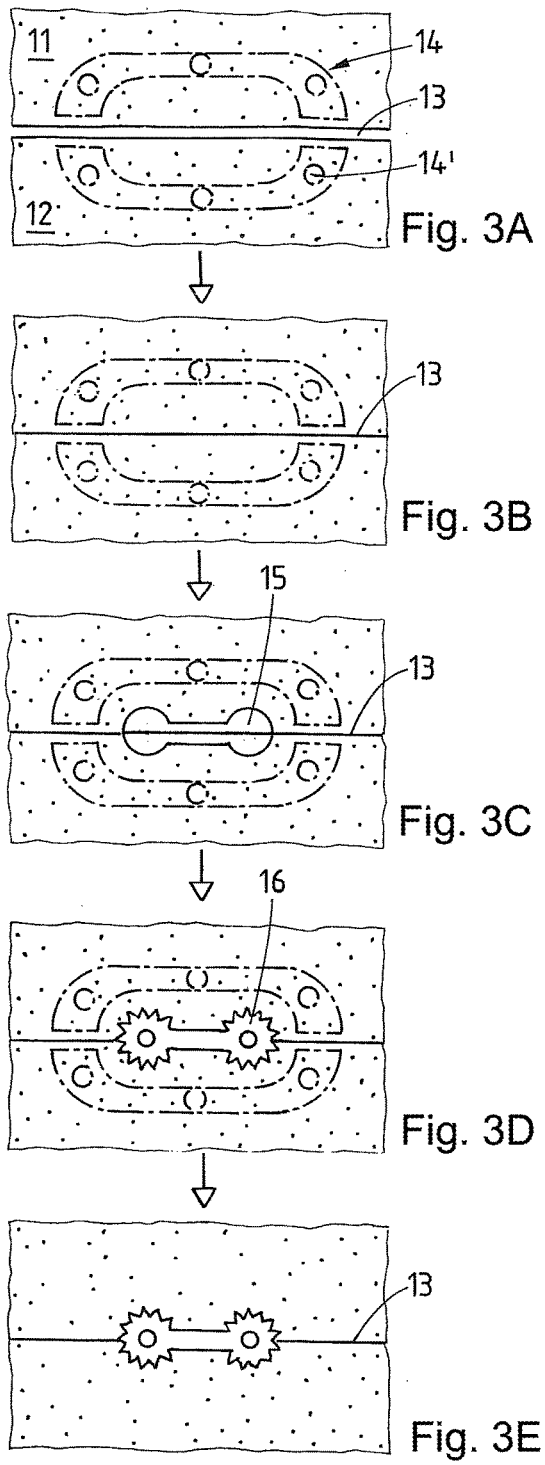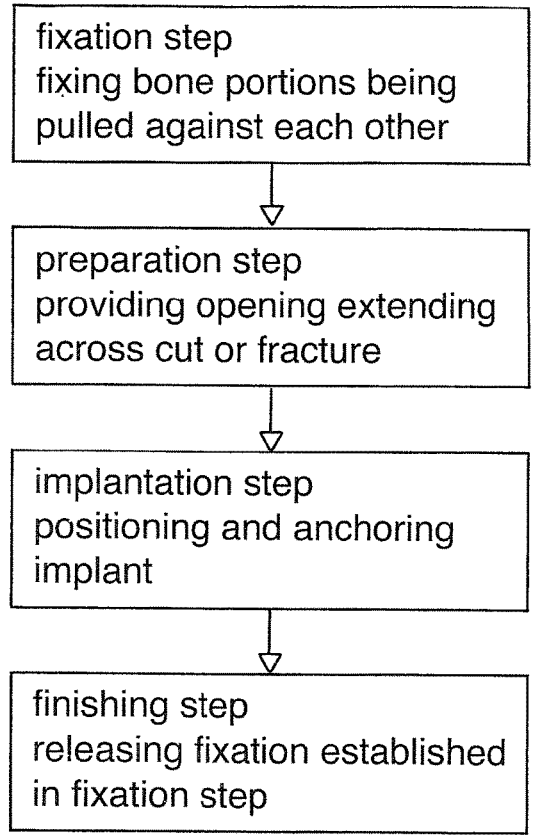
Fig. 4

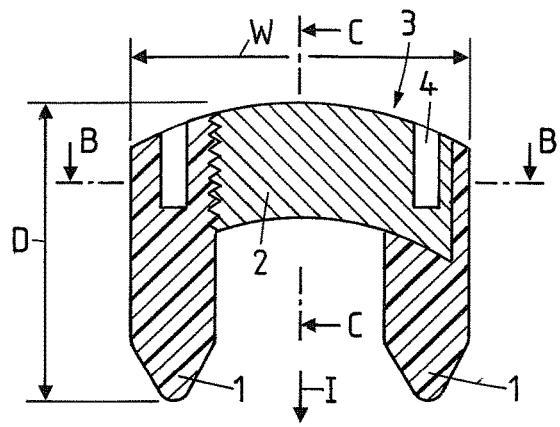
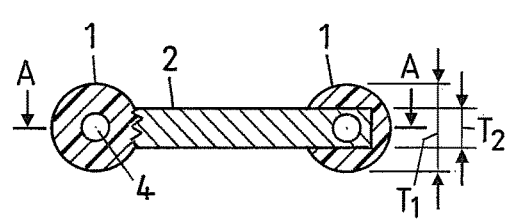
Fig. 8A
Fig. 8B
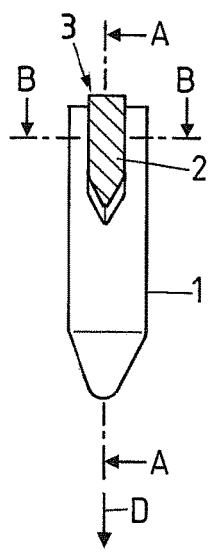
Fig. 8C
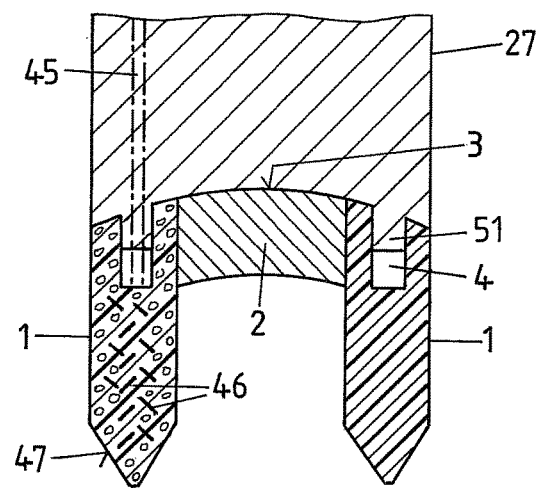
Fig. 9

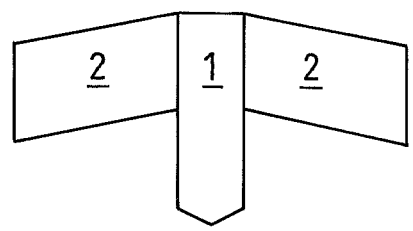
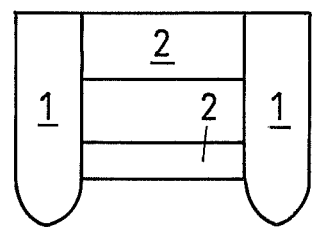
Fig. 16        Fig. 17
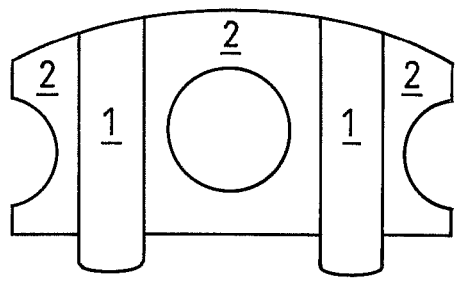
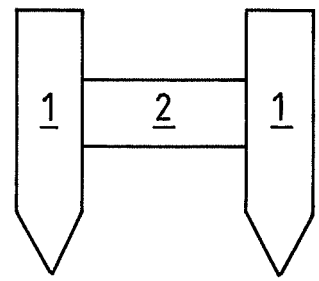
Fig. 18        Fig. 19

METHOD AND IMPLANT FOR STABILIZING TWO BONE PORTIONS SEPARATED BY A CUT OR FRACTURE

BACKGROUND OF THE INVENTION

Field of the Invention

The invention is in the field of medical technology and concerns a method and an implant for stabilizing two bone portions separated by a cut or fracture in a human or animal patient, in particular for stabilizing two bone portions being separated by osteotomy.

Description of Related Art

Osteotomy is a surgical procedure in which a bone is cut with the aim of being shortened, lengthened or re-aligned. Osteotomy is performed on human and animal patients mainly for realigning the load bearing surfaces in joints and for realigning bone portions in particular in the faciomaxillar region but also for re-aligning bone portions healed together with an undesired alignment relative to each other after a fracture. The bone portions separated by the osteotomy procedure mostly need to be re-aligned in a desired position relative to each other and to be stabilized in this position for being able to heal together again. According to the state of the art, osteotomy sites are usually stabilized with the aid of plates (e.g. metal plates) which are positioned on the bone surface across the osteotomy cut and are fastened in this position with the aid of bone screws or nails. According to the state of the art, simple bone fractures are stabilized in the same manner.

The named stabilization of cut or fractured bones with the aid of plates and bone screws is well established but it is of an only limited efficiency, mainly because the plates are preformed and therefore are to be available in a large number of different types for a large number of different applications and different patients. Furthermore, metallic plates and screws need to be removed in most cases, which make further surgery necessary when the cut or fractured bone is healed.

Well known applications of osteotomy concern e.g. human hip or knee joints and serve for re-aligning the articular surfaces of the joint in order to correct dysplasias and deformities by improvement of the alignment and/or the interaction of the articulating bones, or for relieving arthritic pain by re-aligning partly damaged articular surfaces to shift the bearing of the load from damaged to still healthy regions of the articular surfaces. Further well known osteotomy applications concern mandible or maxilla re-alignment e.g. for correcting discrepancies in tooth positions, or concern the chin bone for correcting or improving a person's profile. In veterinary medicine osteotomy is used e.g. for treating canine stifle joints suffering from cranial cruciate ligament rupture or damage, by tibial plateau leveling or tibial tuberosity advancement, both these treatments serving for reducing tibiofemoral shear forces during weight bearing which shear forces become large enough for damaging the joint, when the cranial cruciate ligament is damaged.

BRIEF SUMMARY OF THE INVENTION

It is the object of the invention to provide a further method and an implant for stabilizing, in a human or animal patient, two bone portions separated by a cut or fracture, in particular bones having been subjected to osteotomy or a simple fracture, wherein method and implant according to the invention compared with the state of the art is to allow treatment of a larger number of types of bones, types of patients, and types of cuts and fractures with the same method and the same implant. In addition, the method and implant according to the invention are to be capable of rendering an operation for removing the stabilizing implant unnecessary and they are to be suitable not only for open surgery but in particular for minimally invasive surgery. It is a further object of the invention to create a tool set for carrying out the method according to the invention.

The named objects are achieved by the method, the implant, and the tool set as defined in the independent claims.

The basic idea of the invention is to use instead of the known plate being fixed to the bone surface and reaching across the cut or fracture for stabilizing the two bone portions separated by the cut or fracture, an implant which is positioned in the cut or fracture, i.e. between the bone portions, and anchoring the implant in the bone tissue below the bone surface on both sides of the cut or fracture with the aid of a material having thermoplastic properties and energy (in particular vibrational energy) transmitted into the implant for in situ liquefaction of the material having thermoplastic properties. Therein the material having thermoplastic properties is arranged on the implant such that on liquefaction it flows into the bone tissue on both sides of the cut or fracture where, on re-solidification, it forms a positive fit connection between the implant and the bone tissue and therewith a connection between the two bone portions. In most cases, this connection renders the bone portions stable enough such that additional stabilization measures such as a plate arranged on the bone surface across the cut or fracture and fixed with screws thereon are not needed.

The technique of anchoring an implant in hard tissue such as bone tissue with the aid of a material having thermoplastic properties and vibrational energy transmitted into the implant for in situ liquefaction of the material having thermoplastic properties is disclosed e.g. in the publications U.S. Pat. Nos. 7,335,205, 7,008,226, US 2006/0105295, US-2008/109080, US 2009/131947, WO 2009/109057, and WO 2009/132472. The disclosure of all the named publications and applications is enclosed herein by reference. Therein the thermoplastic material needs to have mechanical properties suitable for a mechanically satisfactory anchorage of the implant in the hard tissue, and, in its liquefied state, a viscosity that enables it to penetrate into natural or beforehand provided pores, cavities or other structures of the hard tissue. Furthermore, an only relatively small amount of the material is liquefied such that no unacceptable thermal load is put on the tissue.

Suitable liquefaction connected with an acceptable thermal loading of the tissue and giving suitable mechanical properties of the positive fit connections is achievable by using materials with thermoplastic properties having an initial modulus of elasticity of at least 0.5 GPa and a melting temperature of up to about 350° C. and by providing such material e.g. on an implant surface, which on implantation is pressed against the hard tissue, preferably by introducing the implant in a hard tissue opening which is slightly smaller than the implant or by expanding the implant in a bone opening which originally is slightly larger than the implant (expansion e.g. by mechanically compressing or buckling the implant). During implantation, the implant is subjected to vibration of a frequency preferably in the range of between 2 and 200 kHz (preferably ultrasonic vibration) by applying e.g. the sonotrode of an ultrasonic device to the implant. Due to the relatively high modulus of elasticity, the thermoplastic material transmits the ultrasonic vibration with such little damping that inner liquefaction and thus destabilization of the implant does not occur, i.e. liquefaction occurs only where the liquefiable material is in contact with the bone tissue and is therewith easily controllable and can be kept to a minimum.

Instead of providing the material having thermoplastic properties on the surface of the implant (disclosed e.g. in U.S. Pat. No. 7,335,205 or 7,008,226), it is possible also to provide the material having thermoplastic properties in a perforated sheath and to liquefy it within the sheath and press it through the sheath perforation to the surface of the implant and into the pores or cavities of the hard tissue (disclosed e.g. in U.S. Pat. Nos. 7,335,205, 7,008,226, WO 2009/109057, and WO 2009/132472) and/or it is possible to liquefy the liquefiable material between two implant parts of which one is vibrated and the other one serves as counter element, the interface between the two implant parts being positioned as near as possible to the bone tissue (as disclosed in US 2009/131947, WO 2009/109057 and WO 2009/132472).

It is possible also to exploit energy types other than vibrational energy for creating the local thermal energy needed for the in situ liquefaction of the material having thermoplastic properties. Such other energy types are in particular rotational energy turned into friction heat in substantially the same manner as the vibrational energy, or electromagnetic radiation (in particular laser light in the visible or infrared frequency range), which radiation is preferably guided through the material with thermoplastic properties and locally absorbed by an absorber being contained in the material having thermoplastic properties or being arranged adjacent to this material (as disclosed in the publications US 2009/131947 and WO2009/109057).

Materials having thermoplastic properties suitable for the device and the method according to the invention are thermoplastic polymers, e.g.: resorbable polymers such as polymers based on lactic and/or glycolic acid (PLA, PLLA, PGA, PLGA etc.) or polyhydroxy alkanoates (PHA), polycaprolactone (PCL), polysaccharides, polydioxanes (PD) polyanhydrides, polypeptides or corresponding copolymers or composite materials containing the named polymers as a component; or non-resorbable polymers such as polyolefines (e.g. polyethylene), polyacrylates, polymetacrylates, polycarbonates, polyamides, polyester, polyurethanes, polysulfones, polyarylketones, polyimides, polyphenylsulfides or liquid crystal polymers LCPs, polyacetales, halogenated polymers, in particular halogenated polyolefines, polyphenylensulfides, polysulfones, polyethers or equivalent copolymers or composite materials containing the named polymers as a component.

Specific embodiments of degradable materials are Polylactides like LR706 PLDLLA 70/30, R208 PLDLA 50/50, L210S, and PLLA 100% L, all of Böhringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in CA Bailey et al., J Hand Surg [Br] 2006 April; 31(2):208-12.

Specific embodiments of non-degradable materials are: Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene, or polycarbonateurethane (in particular Bionate by DSM, in particular type 65D and 75D). An overview table of polymers and applications is listed in Wintermantel, page 150; specific examples can be found in Wintermantel page 161 ff. (PE, Hostalen Gur 812, Höchst AG), pages 164 ff. (PET) 169ff. (PA, namely PA 6 and PA 66), 171 ff. (PTFE), 173 ff. (PMMA), 180 (PUR, see table), 186 ff. (PEEK), 189 ff. (PSU), 191 ff (POM—Polyacetal, tradenames Delrin, Tenac, has also been used in endoprostheses by Protec).

The material having thermoplastic properties may further contain foreign phases or compounds serving further functions. In particular, the thermoplastic material may be strengthened by admixed fibers or whiskers (e.g. of calcium phosphate ceramics or glasses) and such represent a composite material. The material having thermoplastic properties may further contain components which expand or dissolve (create pores) in situ (e.g. polyesters, polysaccharides, hydrogels, sodium phosphates), compounds which render the implant opaque and therewith visible for X-ray, or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed.

Fillers used may include degradable, osseostimulative fillers to be used in degradable polymers, including: β-Tricalciumphosphate (TCP), Hydroxyapatite (HA, <90% crystallinity); or mixtures of TCP, HA, DHCP, Bioglasses (see Wintermantel). Preferred composite materials containing such fillers are: PLDLA (Böhringer: LR706) filled with dibasic calciumphosphate (weight ratio 70:30) and PLLA (Böhringer: L210S) filled with TCP (weight ratio: 40:60).

Osseo-integration stimulating fillers that are only partially or hardly degradable, for non degradable polymers include: Bioglasses, Hydroxyapatite (>90% cristallinity), HAPEX®, see S M Rea et al., J Mater Sci Mater Med. 2004 September; 15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20. Embodiments of bioactive fillers and their discussion can for example be found in X. Huang and X. Miao, J Biomater App. 2007 April; 21(4):351-74), J A Juhasz et al. Biomaterials, 2004 March; 25(6):949-55. Particulate filler types include: coarse type: 5-20 µm (contents, preferentially 10-25% by volume), sub-micron (nanofillers as from precipitation, preferentially plate like aspect ratio >10, 10-50 nm, contents 0.5 to 5% by volume).

Preferred embodiments of the implant according to the invention comprise a plurality of anchoring pins (preferably two), whose proximal ends are connected with each other by at least one bridge portion (preferably one). Such an implant e.g. comprises two anchoring pins equipped for anchorage in the bone tissue using one of the above shortly described anchoring methods, the anchoring pins being connected by a bridge portion, which may be equipped for osseointegration or, the same as the anchoring pins, for anchorage in the bone tissue. Between the distal ends of the anchoring pins, the implant delimits an osteoconduction region, in which the bone tissue of the two bone portions to be stabilized is kept in intimate contact with each other. A proximal implant face is equipped for arranging the implant on a distal end of an implantation tool and for transmitting the energy necessary for the in situ liquefaction into the implant.

For positioning the implant between the two bone portions, these are brought into the desired position relative to each other and in this position are pulled against each other in order to get into intimate contact with each other. Then an opening is made in the bone tissue, the opening reaching across the cut or fracture separating the two bone portions to be stabilized, i.e. a mouth of the opening in the bone surface reaches across the cut or fracture and a depth of the opening extends into the bone tissue substantially along the depth of the cut or fracture. The opening preferably comprises bores for accommodation of the anchoring pins, having a corresponding cross section, and may further comprise a groove for the bridge portion or bridge portions. The implant is then positioned and anchored in the opening. The fixation of the bone portions is released only when the liquefied material has re-solidified in the bone tissue on both sides of the cut or fracture and is therewith able to maintain the bone portions in the desired position and intimate contact with each other.

The groove provided for the bridge portion of the implant may have a depth corresponding to the depth of the bridge portion or, in particular for a bridge portion tapering in a distal direction it may be sufficient to provide a groove which only concerns the cortical layer of the bone portions and to press the bridge portion into the underlying cancellous bone without previous removal of such cancellous bone.

As it is easily possible to make the whole implant from a bio-resorbable or bio-degradable material, the implant may be gradually replaced by new bone tissue bridging the cut or fracture at the place of the implant and therefore the implant does not need to be removed in a second surgical operation. Alternatively the implant may at least partly be made of a non-resorbable or non-degradable material and remain in the bone for permanently fixating the bone portions. This may be particularly advantageous in case of a bone whose healing capacity is impaired by disease (e.g. osteoporosis) or old age.

There is no necessity for the implant according to the invention to comprise any bone or bone replacement material; however, it may of course do so. Bone growth enhancing material such as e.g. allograft or autograft bone material, bone replacement material, sponges, BMP carriers, if used, are preferably arranged in the above named osteoconduction region of the implant, i.e. between the distal ends of the anchoring pins, wherein the named materials may be positioned between the bone tissue of the two bone portions to be stabilized before positioning and anchoring the implant or wherein the named materials may be preassembled with the implant. For such preassembly, implant surfaces around the osteoconduction region may carry retention means such as e.g. grooves or dents for retaining the named material. For accommodation of such materials, it will be advantageous to make room for them between the two bone portions, i.e. to e.g. provide a groove between the bores of the opening in which the implant is to be anchored, the groove having a larger depth than the bridge portion. The bridge portion will serve in such a case for not only stabilizing the anchoring pins relative to each other but also as means for preventing the above named materials from exiting from between the bone portions.

Further embodiments of the implant and the method according to the invention may vary from the above shortly described preferred embodiments as described hereinafter.

The anchoring pins and the bridge portion of the implant constitute separate implant parts (multi-part or preferably three-part implant opposed to the above described one-part implant), wherein the anchoring pins are positioned and anchored in the opening first, and the bridge portion is then mounted on the proximal ends of the anchoring pins, or wherein the bridge portion is positioned in the opening first and the anchoring pins are then pushed through or past the bridge portion and anchored in the bone tissue beside and/or beyond the bridge portion (see FIGS. 13 and 14).

The implant does not comprise a bridge portion, i.e. it comprises only a plurality of anchoring pins (or even only one anchoring pin), wherein a plurality of anchoring pins is preferably implanted simultaneously.

The anchoring pins have any suitable cross sections and the opening parts for accommodating the anchoring pins are not bores but e.g. punched openings.

The bridge portion is plastically or resiliently bendable and the implant is adapted by the surgeon to the form of the cut or fracture by bending the bridge portion.

For stabilizing two bone portions being separated by a cut or fracture, not only one but a plurality of implants is used depending on the application, on the size of the cut or fracture, and on the size of the implant.

The implant does not comprise distinguishable anchoring pins and bridge portions but has the form of a parallelepiped or wedge, a shortest extension extending across the cut or fracture, a longest extension extending along the cut or fracture and a middle extension or tapering extension extending into the cut or fracture, wherein the opening provided for the implant is a corresponding groove.

BRIEF DESCRIPTION OF THE DRAWINGS

The invention is described in further detail in connection with the appended Figs., wherein:

FIG. 3A is a plan view illustrating a first phase of an exemplary embodiment of the method according to the invention;

FIG. 3B is a plan view illustrating a second phase of an exemplary embodiment of the method according to the invention;

FIG. 3C is a plan view illustrating a third phase of an exemplary embodiment of the method according to the invention;

FIG. 3D is a plan view illustrating a fourth phase of an exemplary embodiment of the method according to the invention;

FIG. 3E is a plan view illustrating a fifth phase of an exemplary embodiment of the method according to the invention;

FIG. 4 is a flow chart for the method as illustrated in FIGS. 3A-3E;

FIG. 8A is a sectional elevation view of the implant;

FIG. 8B is a sectional plan view of the implant;

FIG. 8C is a partial sectional elevation view of the implant;

FIG. 9 is a sectional elevation view through a further one-part implant similar to the implants according to FIGS. 1 and 8A to 8C, the implant being mounted on the distal end of an implantation tool;

FIG. 16 is an elevation view of an anchoring pin and bridge portions;

FIG. 17 is an elevation view of anchoring pins and bridge portions;

FIG. 18 is an elevation view of anchoring pins and bridge portions; and

FIG. 19 is an elevation view of anchoring pins and a bridge portion.

DETAILED DESCRIPTION OF THE INVENTION

Figure 1:
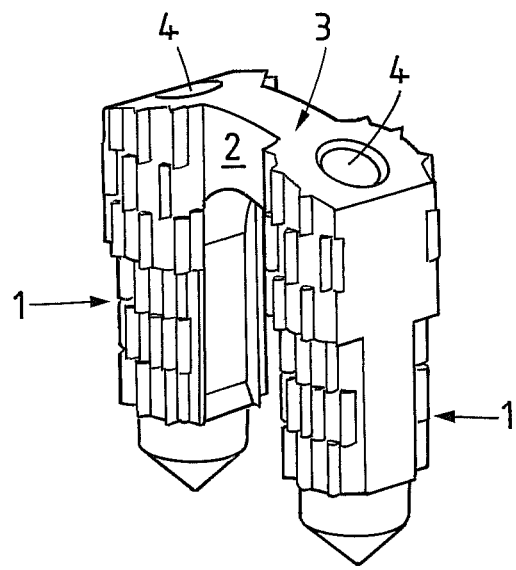
FIG. 1 is a perspective view of a preferred embodiment of the implant according to the invention.

FIG. 1 is a three-dimensional illustration of a preferred embodiment of the implant according to the invention. The implant comprises two anchoring pins 1 and a bridge portion 2, arranged between the proximal ends of the anchoring pins 1. The whole implant is preferably made of a resorbable thermoplastic polymer (e.g. of polylactide, preferably LR706 by Böhringer). The anchoring pins 1 are slightly tapering and comprise a pointed distal end, the surface of the slightly tapering region being equipped with energy directors e.g. in the form of short axial ridges arranged in a plurality of adjacent rings, wherein the ridges of one ring are staggered in relation to the ridges of the adjoining ring or rings. Similar arrangements of energy directors are described in the publication US 2008/0109007 the disclosure of which is enclosed herein by reference.

The opening provided for implantation of the implant according to FIG. 1, which opening reaches across the cut or fracture separating the two bone portions, preferably comprises two bores (possibly stepped) and a groove therebetween (see FIGS. 3A-3E) and is preferably dimensioned such that liquefaction and anchorage between device and bone tissue occurs not only on the surface of the anchoring pins 1 but also on the surface of the bridge portion 2. This means that the implant is slightly oversized in comparison with the opening.

A proximal face 3 of the implant is preferably equipped, e.g. with axially extending bores 4, for holding the implant on the distal end of an implantation tool, as further discussed in connection with following figures. In the case of a fully thermoplastic and therewith x-ray transparent implant it is advantageous to design these openings deeper and to position marker elements therein. These marker elements comprise a material which is visible e.g. for an x-ray control of the implant position after implantation. They consist e.g. of titanium, tantalum or another suitable metal or they comprise a bioresorbable material, such as e.g. a composite material of barium sulfate in PLA, which is eventually resorbed together with the rest of the implant.

If the implant according to FIG. 1 is fully made of a suitable thermoplastic material, in particular of such a material having a relatively low glass transition temperature, it is possible to transmit enough energy into the implant for bringing portions of the material above the glass transition temperature (in addition to liquefying surface material) such that they are capable of being slightly deformed and therefore better adapted to the form of the opening provided for the implantation. Such deformation may e.g. concern the anchoring pins or it may concern the bridge portion.

Figure 2:
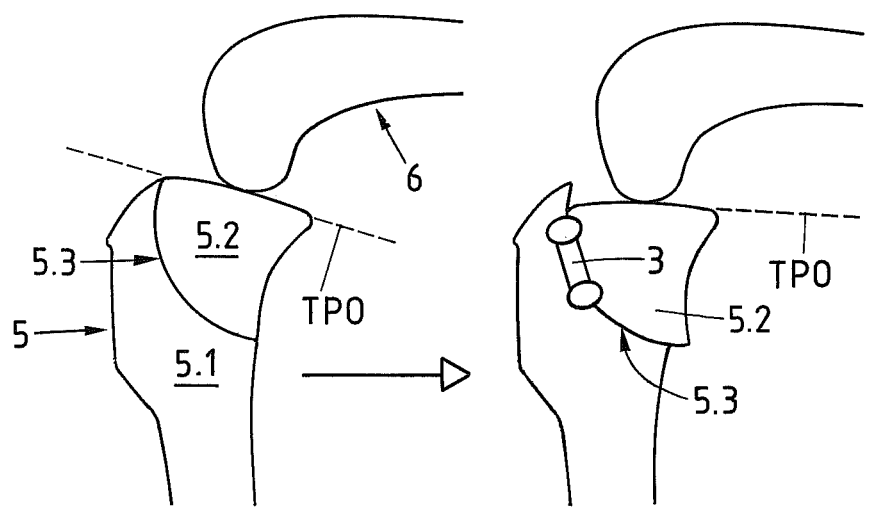
FIG. 2 is an elevation view that shows the method and implant according to the invention used for stabilizing two tibial portions of a canine stifle joint after tibia plateau leveling osteotomy.

FIG. 2 illustrates the application of the method and the device according to the invention for stabilizing two tibial portions of a canine stifle joint after tibia plateau leveling osteotomy. FIG. 2 shows in a very schematic manner, the stifle joint before and after the osteotomy. Visible are the proximal end of the tibia 5 and the distal end of the femur 6, the tibial bone being cut into a distal portion 5.1 and a proximal portion 5.2 by a half circular cut 5.3. The two bone portions 5.1 and 5.2 are re-aligned by rotating the portion 5.2 relative to the portion 5.1 such that the tibia plateau is moved from a backwards sloping position into a substantially horizontal position as indicated with the dashed line denominated with TPO for tibia plateau orientation.

The two bone portions 5.1 and 5.2 are stabilized in the rotated position by implanting an implant into the cut 5.3, the right hand part of FIG. 1 showing the proximal face 3 of an implant according to FIG. 1. Advantageously the implant is implanted in the opening provided for the implantation to a depth such that the proximal implant face 3 is about flush with the bone surface.

FIGS. 3A, 3B, 3C, 3D and 3E illustrate an exemplary embodiment of the method according to the invention in five successive phases, wherein the bone portions 11 and 12 being separated by the cut or fracture 13 are viewed from the bone surface and wherein a distal face of a fixation/guide tool being positioned on the bone surface for the implantation of the implant 15 is illustrated in dash-dotted lines 15 on this bone surface. The implant is similar to the one illustrated in FIG. 1, an exemplary embodiment of the fixation/guide tool is shown in more detail in FIG. 7.

In a first phase shown in FIG. 3A, the bone portions being separated by the cut or fracture 13 have been brought into the desired position relative to each other and the distal face of the fixation/guide tool (lines 14) is fixated on the bone surface, e.g. with the aid of pricks (lines 14') being punched into the bone surface, wherein at least the distal end of the fixation/guide tool comprises two half portions, each one being fixated on one of the bone portions 11 and 12 such that the division between the tool half portions is positioned along the cut or fracture 13.

In a second phase shown in FIG. 3B, the bone portions 11 and 12 are pulled against each other by forcing the two tool half portions towards each other for closing the cut or fracture 13 completely and for bringing the two bone portions into intimate contact with each other which is advantageous for good and fast healing.

In a third phase shown in FIG. 3C, an opening 15 adapted to the implant 16 (phase d) to be implanted between the bone portions 11 and 12 is provided. In the preferred embodiment of the method the opening comprises two bores for accommodating the anchoring pins of the implant and possibly a groove for accommodating the bridge portion of the implant, wherein the groove extends between the two bores, wherein the groove has a lesser depth than the bores, and wherein the bores as well as the groove involve both sides of the cut or fracture, i.e. the cut or fracture 13 between the two bone portions runs approximately diametrically through the bores and approximately midway through the groove.

In a fourth phase shown in FIG. 3D, the implant 16 being adapted to the opening 15 is implanted and anchored in the opening 15, i.e. in bone tissue of both bone portions 11 and 12, such fixating the two bone portions in the desired relative position and in intimate contact with each other.

In a fifth phase shown in FIG. 3E, the fixation/guide tool is removed, and therewith the stabilization procedure according to the invention is completed.

The features of the above described preferred embodiment of the method according to the invention for stabilizing two bone portions being separated by a cut or fracture may be varied e.g. in the following manner without departing from the basic idea of the invention. The bone portions 11 and 12 can be held in intimate contact with each other not by distal half portions of a fixation/guide tool but by per se known means such as e.g. a jig which is installed already for the osteotomy. The implant and the opening may have different forms as discussed already further above.

FIG. 4 is a flow chart illustrating the main steps of the method as illustrated in FIGS. 3A-3E. These main steps are described hereinbelow.

The fixation step includes arranging the two bone portions in a desired position relative to each other, pulling them against each other, such that they are in intimate contact with each other along the cut or fracture, and fixating them in this position.

The preparation step includes providing an opening reaching across the cut or fracture, the form of the opening being adapted to the implant to be used.

The implantation step includes introducing the implant into the opening and applying energy, preferably mechanical vibration, to the implant either during introduction (if the liquefiable material is to be liquefied while being pressed against the bone tissue) or after introduction (if the liquefiable material is to be liquefied inside a perforated sheath and pressed through the sheath perforation and/or if the liquefiable material is liquefied between two device parts).

The finishing step includes releasing the fixation of the two bone portions established in the fixation step.

FIGS. 5A to 5G show the tools of an exemplary embodiment of the tool set according to the invention, the tool set serving for carrying out the method. The tool set is e.g. suitable for implanting an implant as illustrated in FIG. 1 in a method as illustrated in FIGS. 3 and 4. Each tool of the tool set is shown viewed from the side and against the distal tool end. The tools, which are shown in the sequence of their use in the implantation method are the following: a cut finder 20 (FIG. 5A), a fixation/guide tool 21 (FIG. 5B), a drill guide 22 (FIG. 5C), a drill 23 (FIG. 5D), a cutter guide 24 (FIG. 5E), a cutter 25 (FIG. 5F), a control tool 26 (FIG. 5G), and an implantation (preferably vibration) tool 27 (FIG. 5H). Tools 20 and 21 are applicable in the fixation step, tools 21 to 26 in the preparation step, and tools 21 and 27 in the implantation step. The overall axial lengths of the tools is preferably adapted to the application in which they are used. This means that the tools are relatively short when e.g. used on a canine stifle joint, but are longer when used e.g. on a human hip bone.

The cut finder 20 is equipped for finding the cut or fraction between the bone portions and for marking the orientation of this cut or fracture on the bone surface. For this purpose it carries on its distal end at least one flat and preferably blunt protrusion (e.g. two protrusions 30) which is suitable for being pushed into the cut or fracture. The cut finder 20 may further comprise an axial bore 31 for accommodating a K-wire (not shown) being used for locating the cut or fracture to start with, and for guiding the cut finder 20 towards the cut or fracture, wherein the cut finder 20 is pushed along the wire. The cut finder 20 has a cross section with one distinguished larger diameter in the direction of the cut being located with the aid of the distal protrusions or the direction defined by the protrusions respectively (the cross section is e.g. oblong as illustrated or oval but not circular nor square), this cross section being adapted to the implant as well as to inner or outer cross sections of the further tools of the tool set in a way to be elaborated further down.

The fixation/guide tool 21 comprises an axial tunnel 32 for guiding the fixation/guide tool 21 along the cut finder 20, i.e. the tunnel has a cross section which corresponds to the cross section of the cut finder 20. As already discussed in connection with FIGS. 3A-3E, the fixation/guide tool 21 comprises at its distal end two tool half portions 21.1 and 21.2 the section line between the two half portions extending along the distinguished cross section diameter, a distal face of each half portion being equipped with a plurality of short and sharp spikes 33 or blades suitable for fixing the fixation/guide tool to the bone surface on either side of the cut or fracture. As discussed in further detail in connection with FIG. 7, the two distal half portions 21.1 and 21.2 of the fixation/guide tool 21 are designed to resiliently flare outwards, such that in a non-stressed configuration there is a gap between the distal faces of the two half portions. In the fixation step, the spikes are forced into the bone surface e.g. by applying a punch 34 to the proximal tool end. Then the two half portions are forced against each other for pulling the bone portions fixed thereon against each other (see FIG. 7) and the half portions are locked in the forced position for keeping the bone portions in intimate contact with each other.

The drill guide 22 comprises two axial bores 35 adapted in diameter and distance from each other to the diameter and the position of the anchoring pins of the implant. The outer cross section of the drill guide 22 is adapted to the cross section of the axial tunnel 32 of the fixation/guide tool 21 such that guidance of the drill guide 22 in this axial tunnel positions the two axial bores on the distinguished diameter and therewith over the cut or fracture. The drill guide 22 further comprises a stop shoulder 36, e.g. at its proximal end or inside the axial bores.

The drill 23 being equipped for drilling bone tissue has a diameter being adapted to the diameter of the axial bores 35 of the drill guide 22 and an axial length from a distal end to a depth stop, e.g. a region of increasing diameter 37, which axial length is greater than the axial length of the drill guide from a distal end to the stop shoulder 36 by about the depth to which the anchoring pins of the implant are to be introduced in the bores made with the drill.

The cutter guide 24 has substantially the same outer cross section as the drill guide 22 and comprises an axial tunnel 38 which has an oblong cross section extending along the distinguished diameter and being adapted to the proximal face of the bridge portion of the implant. The cutter guide 24 further comprises a stop shoulder 39, e.g. on its proximal end as illustrated, or inside the axial tunnel 38.

The cutter 25 is preferably a rotating tool equipped for removing bone tissue from between the two bores produced with the aid of the drill guide 22 and the drill 23. The cutter 25 is e.g. a drill having a cross section adapted to the smaller extension of the cross section of tunnel 38 and preferably being mounted to a rotational drive such that it can be laterally displaced or pivoted relative to a housing of the drive in the plane of the longer extension of the cross section of tunnel 38 in a very limited manner. The cutter may also be designed as a correspondingly shaped punching tool being e.g. driven by ultrasonic vibration. Such punching tools are disclosed in the publication US 2008/269649, the disclosure of which is enclosed herein by reference. The cutter 25 further comprises a depth stop 40 cooperating with the stop shoulder 39 of the cutter guide 24. The axial length of the cutter 25 from its distal end to the depth stop 40 is larger than the axial length of the cutter guide 24 from its distal end to the stop shoulder 39 by the depth to which the tissue between the two bores is to be removed, preferably at least by the depth of the bridge portion of the implant.

The control tool 26 has a distal end similar to the implantation tool 27 carrying the implant (see below) but slightly undersized and, adjoining this distal end, it has a cross section which is the same as the outer cross section of drill guide and cutter guide. The control tool 26 advantageously carries depth marks (not shown) where it protrudes from the fixation/guide tool 21, the marks indicating depths to which the distal end of the control tool is introduced in the opening produced with the drill 23 and the cutter 25.

The implantation tool 27 is e.g. a sonotrode which is equipped for being coupled to a vibration drive, e.g. of an ultrasonic device. The distal end of the implantation tool 27 is equipped for holding the implant 16 and for transmitting energy (e.g. vibration) to the implant. For the latter function, it is preferable for the distal face of the implantation tool 27 to be adapted exactly to the proximal face of the implant 16. In an area between the distal end and the proximal end, the implantation tool has a cross section which is substantially the same as the outer cross section of the drill guide 22, of the cutter guide 24 and of the control tool 26. The implantation tool 27 may comprise a depth stop 41 like the drill 23 and the cutter 25, which depth stop 41 cooperates e.g. with the proximal face of the fixation/guide tool 21 or with a corresponding stop shoulder inside the axial tunnel 32 of the fixation/guide tool. For giving the surgeon more freedom regarding implantation depth it may be advantageous to not equip the implantation tool 27 with a depth stop but rather with one or a plurality of depth marks (not shown) which show the surgeon how deep the implant is introduced in the opening at any moment during implantation.

It is also possible to design the combination of implantation tool 27, implant 16 and fixation/guide tool 21 or part thereof as a load frame containing a biased spring which is released for the implantation step to provide the axial force and stroke necessary for the implantation step. Suitable such load frames are disclosed in publication WO 2009/109057, the disclosure of which is enclosed herein by reference.

Figure 5:
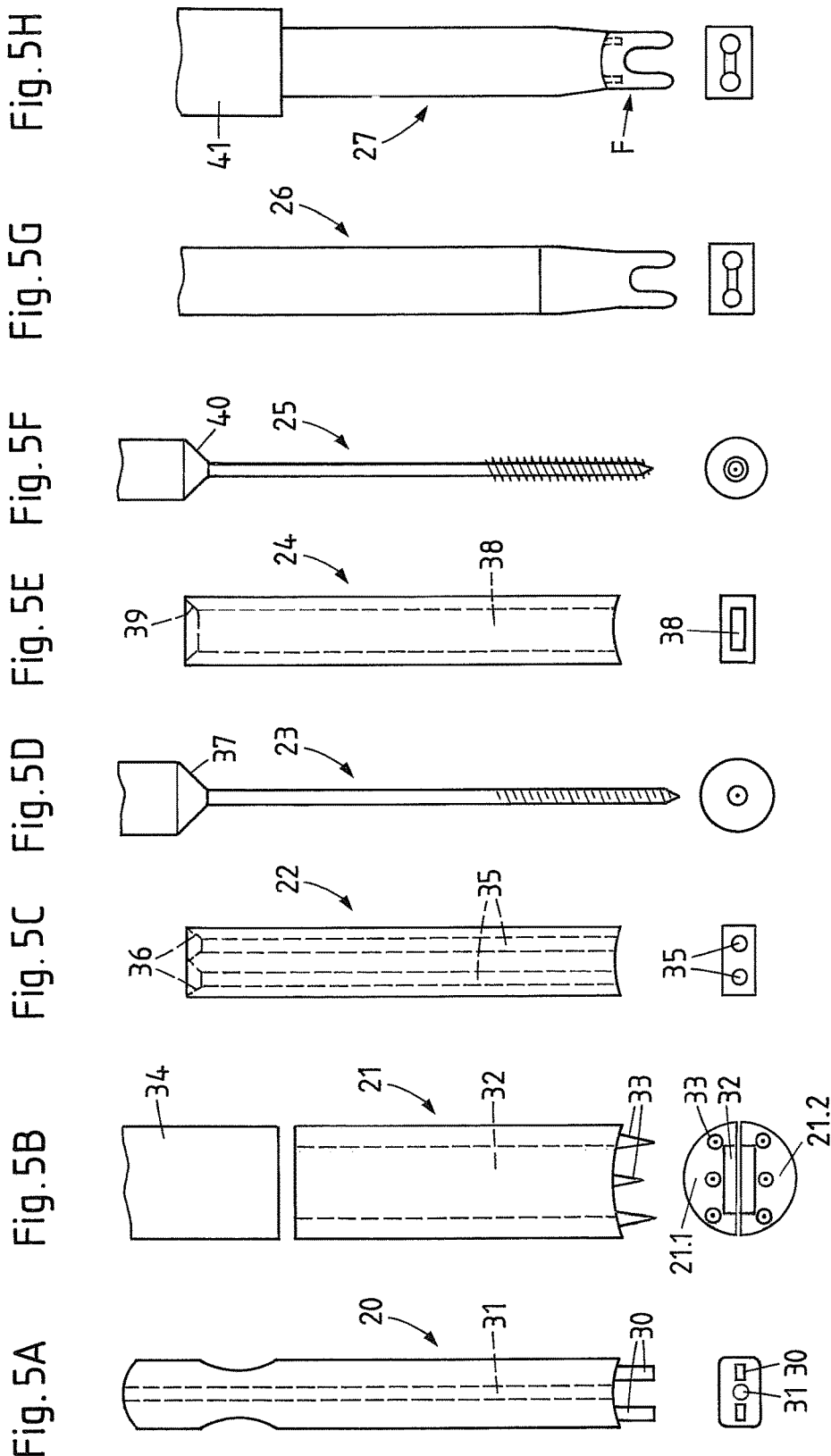
FIG. 5A is an elevation view of a cut finder.
FIG. 5B is an elevation view of a fixation/guide tool.
FIG. 5C is an elevation view of a drill guide.
FIG. 5D is an elevation view of a drill.
FIG. 5E is an elevation view of a cutter guide.
FIG. 5F is an elevation view of a cutter.
FIG. 5G is an elevation view of a control tool.
FIG. 5H is an elevation view of an implantation tool.
Figure 6:
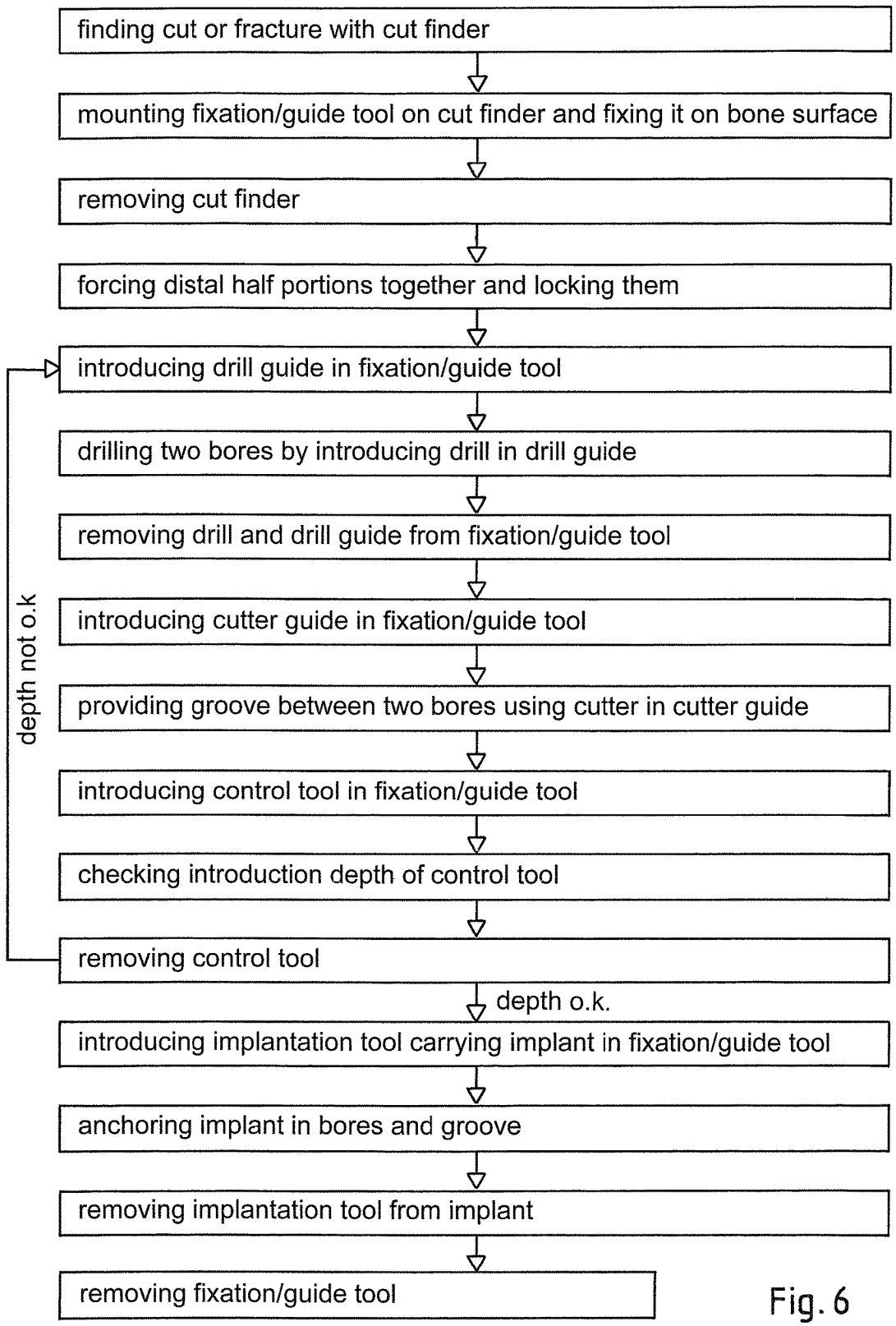
FIG. 6 is a flow chart of a method in which the whole tool set according to FIGS. 5A to 5H is used.

Implantation of the implant according to FIG. 1 in a preferably minimally invasive or mini-open procedure with the aid of the tool set according to FIGS. 5A to 5H comprises the following steps, which are schematically illustrated in the flow diagram of FIG. 6. The steps are described hereinbelow.

Finding and marking the cut or fracture between the two bone portions by positioning the protrusions 30 of the cut finder 20 in the cut or fracture, wherein the cut finder 20 is possibly introduced along a previously positioned K-wire.

Positioning and fixing the fixation/guide tool 21 on the bone surface each distal half portion on one of the bone portions by introducing the cut finder 20 into the axial tunnel 32 of the fixation/guide tool 21, by pushing the fixation/guide tool 21 against the bone until it abuts the bone surface, and by punching the spikes 33 or blades of the fixation/guide tool 21 into the bone surface using the punch 34.

Removing the cut finder 20.

Forcing the distal half portions of the fixation guide tool 21 against each other and locking them in the forced position.

Positioning the drill guide 22 in the axial tunnel 32 of the fixation/guide tool 21, making sure that its distal face abuts on the bone surface.

Positioning the drill 23 in one of the axial bores 35 of the drill guide 22, drilling the first bore and repeating positioning and drilling for the second bore, wherein the predefined depth of the bores is reached when the depth stop 37 of the drill 23 abuts on the stop shoulder 36 of the drill guide 22.

Removing the drill 23 and the drill guide 22 from the fixation/guide tool 21.

Positioning the cutter guide 24 into the axial tunnel 32 of the fixation/guide tool 21 making sure that its distal face abuts on the bone surface.

For cutting a groove between the bores, positioning the cutter 25 into the axial tunnel 38 of the cutter guide 24 and activating it and, if applicable, moving it laterally in the axial tunnel 38 of the cutter guide 24, wherein the predefined depth of the groove is reached when the depth stop 40 of the cutter 25 abuts on the stop shoulder 39 of the cutter guide.

Removing the cutter 25 and the cutter guide 24 from the fixation/guide tool 21.

Controlling the accuracy of bores and groove by introducing the control tool 26 into the axial tunnel of the fixation/guide tool 21 and checking the introduction depth and removing the control tool.

If the controlled introduction depth is not o.k., repeating the steps of introducing the drill guide 22, of introducing the drill 23 and of drilling, the steps of introducing the cutter guide 24, of introducing the cutter 25 and of cutting the groove, and the steps of introducing the control tool 26 and of checking the introduction depth.

If the controlled introduction depth is o.k., introducing the implantation tool 27 with the implant 16 mounted to its distal end into the axial tunnel 32 of the fixation/guide tool 21 and transmitting energy through the implantation tool 27 and into the implant 16 while introducing the implant into the bores and groove, wherein a predetermined depth of introduction is reached when the depth stop 41 of the implantation tool 27 abuts on the proximal face of the fixation/guide tool 21 or a freely selectable introduction depth is reached when a corresponding mark on the implantation tool has reached the proximal face of the fixation/ guide tool 21. Separating the implantation tool 27 from the anchored implant 16 and removing it from the fixation/guide tool 21.

Removing the fixation/guide tool 21.

The step of finding the cut or fracture using the cut finder and the step of controlling the bores and groove using the control tool are not obligatory steps.

In a preferred tool set, the tools have the following further features, which may cooperate with further tools: For x-ray control of the correct position of its distal protrusions in the cut or fracture, the cut finder 20 (except for its distal protrusions) should have a sufficient transparency for x-rays through its length and at the same time needs a sufficient mechanical stiffness. Therefore it is proposed to e.g. manufacture the cut finder 20 of PEEK and to increase its transparency by providing a plurality of through openings along its length, or to manufacture it as a sandwich construction with two relatively thin rigid surface layers (e.g. made from carbon or glass fiber reinforced laminates) oriented parallel to the longer extension of the cross section and a center layer of foamed material (e.g. polyurethane foam) for better transparency. The fixation/guide tool 21 is designed to have a first axial length and in the region of its proximal end it comprises means for removeably fixing a laterally extending handle piece. The cut finder 20 has an axial length which is greater than the first axial length and it comprises a through opening situated beyond the proximal face of the fixation/guide tool 21 when the cut finder 20 is positioned in the fixation/guide tool. For removing the cut finder 20 from the fixation/guide tool 21, the distal end of an angled remover tool (not illustrated) is introduced into the through opening and is pivoted upwards while the remover tool is supported on the proximal face of the fixation/guide tool 21. The punch 34 has an axial channel of the same cross section as the axial channel of the fixation/guide tool 22 and an axial length such that the fixation/guide tool 21 and the punch 34 together have and axial length which is larger than the axial length of the cut finder 20 such that the punch 34 can be positioned over the proximal end of the cut finder being positioned in the fixation/guide tool 21. The drill guide 22 and the cutter guide 24 have proximal flanges which rest on the proximal face of the fixation/guide tool 21 when the distal end is positioned against the bone surface.

Figure 7:
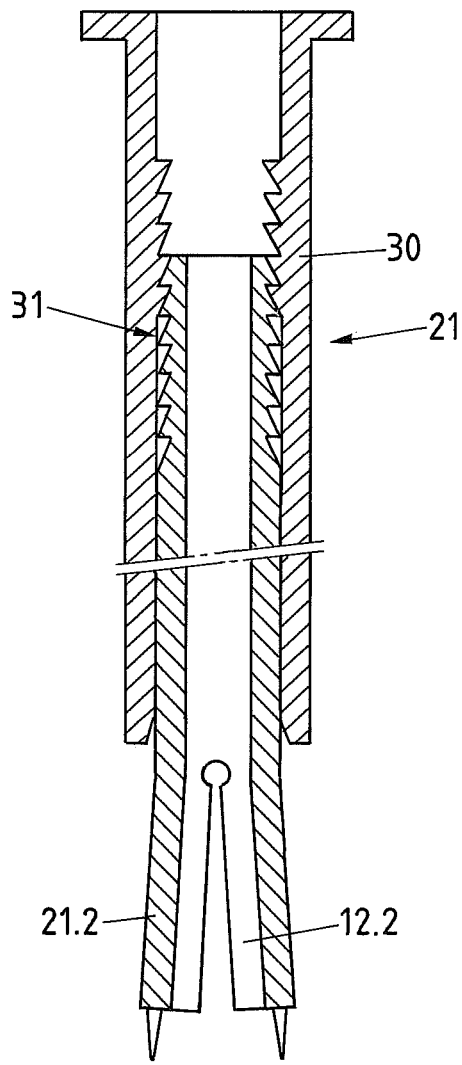
FIG. 7 is a sectional elevation view that shows an exemplary embodiment of the fixation/guide tool as used in the method according to the invention for fixating the bone portions separated by the cut or fracture and for pulling the bone portions against each other.

FIG. 7 is an axial section through an exemplary embodiment of the fixation/guide tool 21. In this figure the resiliently outward flaring distal half portions 21.1 and 21.2 are visible as well as a forcing sleeve 30 with an inner cross section being slightly larger than the outer cross section of the fixation/guide tool 21 at its proximal end but smaller than the distal face of the fixation/guide tool 21 when the half portions are in their outward flaring, i.e. non-forced position. The distal half portions 21.1 and 21.2 are forced against each other by moving the forcing sleeve 30 in a distal direction, forcing the outwards flaring half sections against each other. The movement of the forcing sleeve 30 relative to the fixation/guide tool 21 and its final position are locked by e.g. a ratchet system 31 comprising two meshing linear racks with asymmetrical teeth, one rack arranged on the outside of the fixation/guide tool 12, the other one on the inside of the forcing sleeve 30. Any other per se known measure allowing movement of the forcing sleeve relative to the fixation/guide tool 21 in one direction only or at least being able to lock the forcing sleeve 30 in a final position are applicable also. If the forcing sleeve 30 protrudes beyond the proximal face of the fixation/guide tool 21, the forcing sleeve can be moved distally using a suitable punch (not shown).

FIGS. 8A to 8C show a further exemplary embodiment of the implant according to the invention, whose form is quite similar to the form of the implant according to FIG. 1. FIG. 8A shows the implant in section perpendicular to its thickness T (parallel to the implantation direction I; section line A-A in FIGS. 8B and 8C), FIG. 8B shows the implant in section perpendicular to its depth D (implantation direction I perpendicular to the paper plane; section line B-B in FIGS. 8A and 8C), and FIG. 8C shows the implant in section perpendicular to is width W (parallel to the implantation direction I; section line C-C in FIGS. 8A and 8B).

The implant comprises two anchoring pins 1 and a bridge portion 2 situated between the two anchoring pins 1. The anchoring pins 1 have preferably a larger depth D and a larger thickness T1 than the bridge portion 2.

The bridge portion 2 is e.g. made of a non-liquefiable (in the sense of the anchoring technique) material, e.g. of a metal (e.g. titanium or titanium alloy), of a ceramic material (e.g. zirconium oxide) or of a thermoset polymer or thermoplastic polymer (e.g. PEEK) having a melting temperature, which is sufficiently higher than the melting temperature of the thermoplastic material comprised by the anchoring pins 1 which is to be liquefied. The bridge portion may also be made of a composite material comprising e.g. a trabecular metal (e.g. titanium or tantalum) and a thermoset or thermoplastic polymer. A composite material comprising endless fibers (e.g. carbon fibers) molded into a plastic material (e.g. PEEK OPTIMA Polymer™) with the aid of the composite flow molding process by the Swiss firm "icotec" is a further suitable material for the bridge portion. Non-resorbable polymeric or composite materials used for the bridge portion are preferably equipped with osseointegration supporting means like e.g. a coating of hydroxy apatite.

The anchoring pins 1 comprise the thermoplastic material to be liquefied at least on their surfaces to come into contact with the bone tissue or are e.g. made of this material, wherein, if the anchorage is to be achieved with the aid of mechanical vibration, the named surfaces preferably comprise energy directors (not shown) e.g. in the form of protruding humps or axial ridges. The anchoring pins 1 are joined to the bridge portion 2 by adhesion or, as illustrated on the left hand side of the implant of FIG. 8A, via a rough surface or surface structure suitable for forming together with the liquefiable material a positive fit connection. For a stronger connection between the anchoring pins 1 and the bridge portion 2 the latter may reach into or through the anchoring pins 1 as illustrated on the right hand side of the implant of FIG. 8A. The implant is manufactured by e.g. positioning the bridge portion 2 into a corresponding mold and injection-molding the anchoring pins 1 to or around the bridge portion 2.

The implant embodiment as illustrated in FIGS. 8A to 8C may further comprise an edge portion (not shown) connecting the two proximal ends of the anchoring pins 1 and covering the proximal face and possibly up to about 20% of the depth of the bridge portion 12 and consisting of the liquefiable material. Such an edge portion of an implanted implant constitutes a polymer seam tightly closing the cut or fracture. In a further embodiment of the implant similar to the one shown in FIGS. 8A to 8C the bridge portion as well as the anchoring pins are made entirely of the liquefiable material (see also FIG. 1).

The proximal face 3 of the implant is preferably adapted to the bone surface by e.g. being curved. As discussed already in connection with FIG. 1, the proximal face 3 preferably comprises means for the implant to be held by the implantation tool. Such means are e.g. axial openings or bores 4 arranged e.g. in the region of the anchoring pins 1 and cooperating with corresponding protrusions provided on a distal tool face (see also FIG. 5H).

For an exemplary embodiment of the implant, the two thicknesses T1 (anchoring pin) and T2 (bridge portion) are e.g. in the range of 1 to 3 mm and 3 to 8 mm, the overall depth D is in the range of 5 to 20 mm, preferably 7 to 20 mm, the overall width W in the range of 5 to 20 mm, preferably 5 to 15 mm.

FIG. 9 is an axial section on a larger scale than FIG. 5H of the distal end of the implantation tool 27 and an implant similar to the one illustrated in FIGS. 8A to 8C being mounted thereon for implantation. The implant is held on the distal tool end by protrusions 51 extending from the distal tool face and being adapted to enter the openings 4 in the proximal face 3 of the implant. As already mentioned further above, for optimal transfer of vibrational energy to the implant and therewith optimal anchorage of the implant in the bone tissue it is preferable that the form of the distal tool face matches the form of the proximal face 3 of the implant as exactly as possible, such enabling transfer of the vibration from the tool 26 to the implant over the whole distal tool face.

The implant according to FIGS. 1, 8A to 8C and 9, the implantation method according to FIGS. 3, 4 and 6 and the tool set according to FIGS. 5A to 5H can be modified in e.g. the following manner, without departing from the basic idea of the invention.

The bridge portion 2 of the implant is bent or bendable to be not straight and non-parallel to the device width W, the implant therewith being adapted or adaptable to better fit curved cuts or fractures (necessitates corresponding adaptation of the drill guide 22, the cutter guide 24, the control tool 26 and the implantation tool 27, and possibly of the cut finder 20 such that the protrusions 30 define a curved line instead of a straight line).

Both the anchoring pins 1 and the bridge portion 2 of the implant are substantially made of a liquefiable material (see FIG. 1), wherein the implant portions may be made of the same liquefiable material or different such materials, and wherein the bridge portion 2 may carry a coating of a material which is capable of enhancing osseointegration. Such coating may e.g. comprise calciumphosphate or apatite.

Both the anchoring pins 1 and the bridge portion 2 are made substantially of a non-liquefiable material, e.g. of titanium or a titanium alloy or of a ceramic material. The non-liquefiable material is preferably treated to have a surface structure, which in the region of the bridge portion 2 enhances osseointegration and which in the region of the anchoring pins 1 is suitable for adherence of an at least partial coating comprising the liquefiable material. Anchoring pins comprising a metal core have the advantage of being visible with X-ray and therewith facilitating implantation. Such cores may also be removable after implantation.

The anchoring pins 1 have non-round cross sections (may necessitate adaptation of the drill guide 22 and possibly of the drill 23, which may be replaced by e.g. a vibration driven punching tool as disclosed in the publication US 2008/269649).

The proximal implant face is not adapted to a curved bone surface but is e.g. straight and extending e.g. perpendicular to the implantation direction (necessitates corresponding adaptation of the distal face of the implantation tool 27).

The proximal face of the anchoring pins 1 does not comprise openings 4 adapted to corresponding protrusions 51 of the implantation tool 27 but vice versa, or this proximal face is even. Further means and ways for attaching the implant to the distal end of the implantation tool are disclosed in the above named publications U.S. Pat. Nos. 7,335,205 and 7,008,226.

The distal regions of the anchoring pins 1 and/or of the bridge portion 2 are not tapering or the anchoring pins 1 and/or the bridge portion 2 taper continuously or in steps over their whole depth, i.e. from the proximal face to their distal end (necessitates corresponding adaptation of the drill 23 and possibly of the drill guide 22).

The difference in thickness between the anchoring pins 1 and the bridge portion 2 is small (<1 mm) and/or the anchoring pins are equipped with self-reaming structures, such enabling implantation without the necessity of providing bores (use of the drill guide 22 and the drill 23 may be eliminated, adaptation of the cutter guide 24 may be necessary).

No groove between the two bores is provided for the bridge portion 2 (use of the cutter guide 24 and the cutter 25 may be eliminated).

Figure 13:
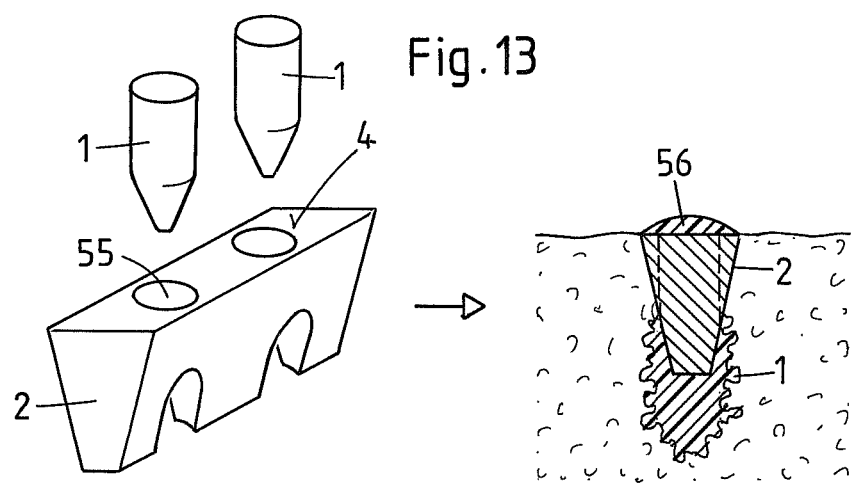
FIG. 13 is a perspective view and a sectional elevation view that show a further exemplary embodiment of the implant according to the invention, the implant comprising three separate parts to be introduced in the joint in succession and to be assembled within the joint (three-part or multi-part implant)
Figure 14:
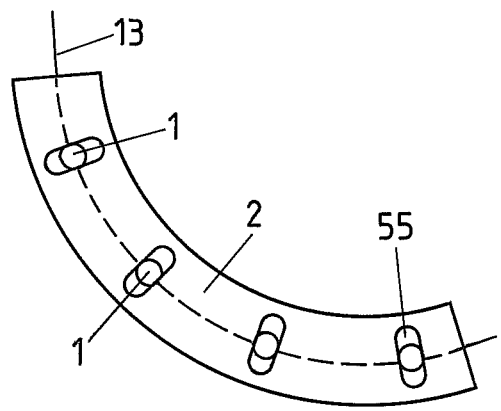
FIG. 14 is a plan view that illustrates an exemplary application of the implant according to FIG. 13.

The implant is a three-part (or multi-part) implant comprising two (or more than two) anchoring pins and one bridge portion constituting three (or more than three) separate implant parts, wherein the bridge portion is first positioned in the cut or fracture and the anchoring pins are then pushed through or past the bridge portion to be anchored in the bone tissue and possibly in the bridge portion (see also FIGS. 13 and 14; necessitating a second implantation tool being equipped for energy transmission or not, depending on whether the bridge portion comprises a liquefiable material and is to be anchored in the tissue, or whether the bridge portion is made of a non-liquefiable material and is impacted into the groove provided for it or into the cut or fracture).

The implant is a three-part implant comprising two anchoring pins and one bridge portion constituting three separate device parts, wherein the anchoring pins are first implanted (preferably simultaneously) and the bridge portion is then fixed to the two proximal faces of the implanted anchoring pins (necessitating a second implantation tool being equipped for energy transmission or not, depending on whether the bridge portion comprises a liquefiable material and is fixed to the anchoring pins by e.g. ultrasonic welding, or whether the bridge portion is made of a non-liquefiable material and is impacted into the proximal faces of the implanted anchoring pins).

The implant comprises two separate anchoring pins and no bridge portion, wherein the two anchoring pins are preferably implanted simultaneously (use of cutter guide 24 and cutter 25 can be eliminated).

The implant comprises one anchoring pin and no bridge portion (drill guide 22 and implantation tool 27 may possibly be adapted, use of cutter guide 24 and cutter 25 can be eliminated).

The one- or three-part implant is anchored in the bone tissue using electromagnetic radiation (preferably in the visible or infrared frequency range) for liquefaction of the liquefiable material. For this purpose, instead of the implantation tool 27 being a vibration tool, the implantation tool having the same form as the vibration tool but further comprises light guides with proximal ends being connected to a radiation source (e.g. laser) and distal ends arranged at the distal tool face in a manner suitable for coupling the laser light into the anchoring pins of the implant. Furthermore, the anchoring pins are designed to comprise in a central region a material which is transparent for the laser light and capable of scattering it and near the surfaces where liquefaction is to occur a material capable of absorbing the laser light for creating the thermal energy needed for the liquefaction and anchoring. The anchoring pins consist e.g. of one thermoplastic material which in a pure state is transparent for the laser light and which in the central region contains a scattering agent and in a peripheral region an absorbing agent, the agents being e.g. particulate or molecular. In FIG. 9, the left hand side of the tool is shown comprising a light guide 45 (dash-dot lines) and the left hand anchoring pin comprising a central region 46 with a scattering agent (indicated by short lines of varying orientation) and a surface region 47 with an absorbing agent (indicated by small circles). The two agents need to be adapted in a per se known manner to the electromagnetic radiation to be coupled into the anchoring pin. The radiation source is activated shortly before, during or after the implant is positioned in the opening. During liquefaction, a pressing force is applied to the implantation tool for making the liquefied material to penetrate into the bone tissue.

Figure 10:
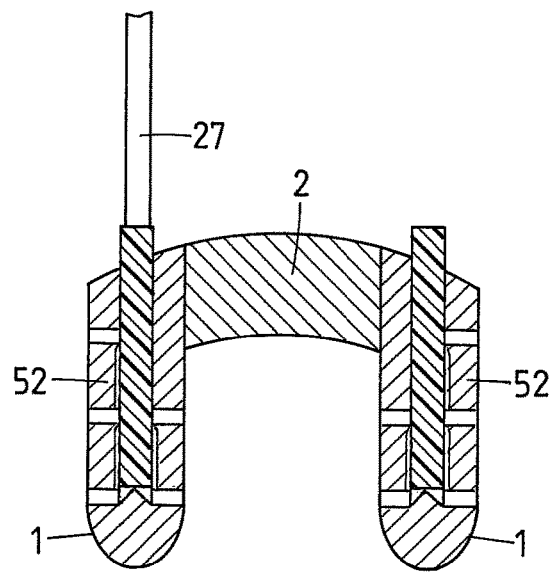
FIG. 10 is a sectional elevation view of a further exemplary embodiment of a one-part implant similar to the implants of FIGS. 1 and 8A to 8C.

FIG. 10 shows a further exemplary embodiment of the implant according to the invention. The implant has approximately the same form as the implant shown in FIG. 1 or 8A to 8C, but the anchoring pins 1 do not consist fully of the liquefiable material or comprise this material on their surfaces but they comprise a perforated sheath 52 each and the liquefiable material is provided inside these sheaths 52, e.g. in the form of a polymer pin.

The method for implanting the implant as shown in FIG. 10 is different from the method for implanting the implant as shown in FIGS. 1 and 8A to 8C in that the implant needs to be positioned in the opening provided for it and only then the liquefiable material is liquefied by being pressed into the sheath 52 and simultaneously energy being transmitted into it. On liquefaction the material is pressed through the perforated walls of the sheaths 52 to penetrate into the bone tissue in the liquid state. For such liquefaction and pressing out, the implantation tool 27 equipped for transmitting energy is applied to the liquefiable material only, which implantation tool 27 may comprise a forked distal end equipped for holding and guiding the implant on being introduced into the opening and for transmitting energy to the liquefiable material of both anchoring pins 1 simultaneously. It is also possible to employ separate implantation tools for positioning the implant and for transmitting energy to the liquefiable material and pressing it into the sheathes, wherein the implantation tool for the latter purpose may have one only distal end (as illustrated) and the two anchoring pins are anchored in the bone tissue one after the other.

It is also possible to use vibrational energy not only for liquefying the liquefiable material contained in the sheaths 52 but also for facilitating the positioning of the implant according to FIG. 10 in the opening provided for it, which is achieved by using an additional vibration tool (not shown) suitable for transmitting the vibration to the sheaths of the anchoring pins and/or to the bridge portion (vibration tool 27 e.g. as shown in FIG. 9).

It is also possible to first position the implant in the opening provided for it without the liquefiable material being present in the sheaths 52 using a corresponding implantation tool and only then introducing the liquefiable material constituted by two polymer pins adapted to the inner cross section and length of the sheaths 52 and transmitting the energy thereto using a further implantation tool.

The embodiment as shown in FIG. 10 allows also using a bone cement instead of the liquefiable material, or a polymer of a high viscosity, wherein the cement or polymer is made to harden or cure when pressed out of the sheath and into the bone tissue.

Instead of e.g. vibrating the liquefiable material positioned in the sheaths 52 it is possible also to couple a pin comprising the liquefiable material to a rotation drive, to introduce a distal portion of the pin into the sheath 52 and to liquefy the material by rotating the pin within the sheath 52 and at the same time pressing it into the sheath and holding the sheath for preventing it from rotating with the rotating pin, such creating friction at least at the distal pin end and therewith thermal energy which liquefies the pin material.

Furthermore, as already mentioned in connection with the implant according to FIGS. 8A to 8C and 9, it is possible also to couple, instead of vibrational or rotational energy, electromagnetic radiation (preferably of the visible or infrared frequency range) into the liquefiable material which is e.g. equipped for scattering the radiation and transmitting it into the sheath (e.g. made of metal) where it is absorbed to create thermal energy which is able to liquefy the thermoplastic material at least partly. Absorption may also take place within the pin which for this purpose contains an absorbing agent. It is possible also to design the sheath such that at least an inner surface thereof can be heated electrically.

Figure 11:
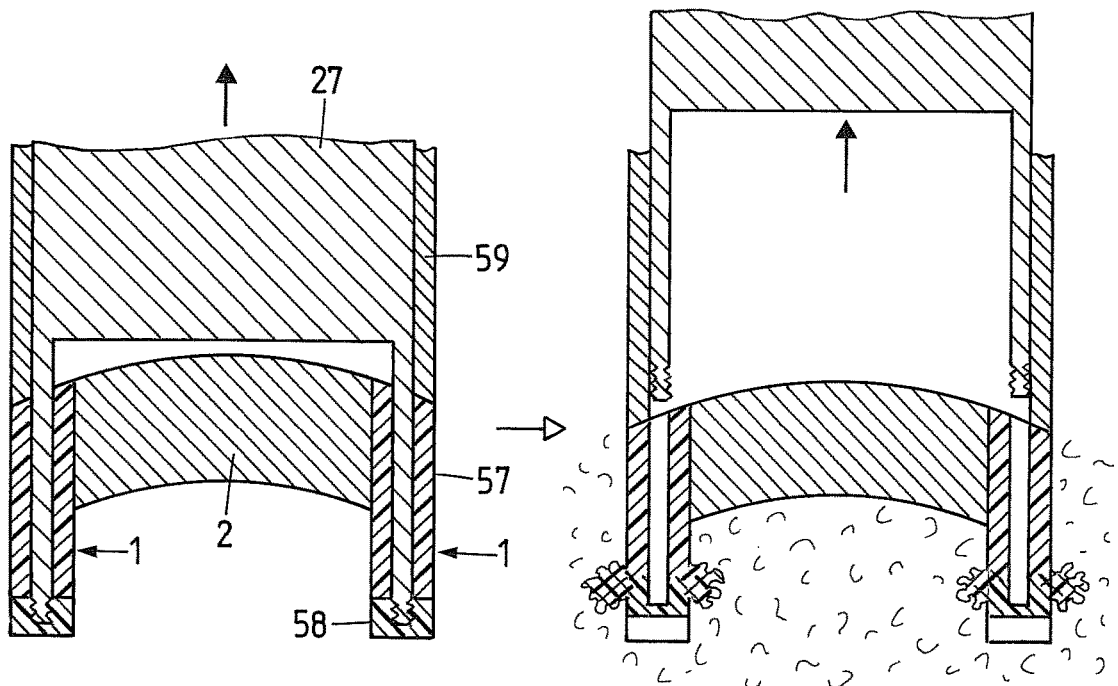
FIG. 11 is a sectional elevation view of a further exemplary embodiment of a one-part implant similar to the implants of FIGS. 1 and 8A to 8C.

FIG. 11 shows a further exemplary embodiment of the implant according to the invention and the distal end of an implantation tool 27 suitable for implantation of the implant. The anchoring pins 1 of the implant are anchored in the bone tissue using the anchoring technique as described in the publication WO 2009/055952. The anchoring pins 1 have the form of polymer tubes 57 and distal ends of the implantation tool 27 protrude through the tubes 57 and, adjacent to the distal ends of the tubes, carry distal foot pieces 58 which consist of the same polymer material as the tubes 57 or of a different polymer material being weldable to the polymer material of the tubes. This is shown on the left hand side of FIG. 11.

The foot pieces 58 are fixed to the implantation tool 27 via a connection (e.g. threads) which is able to transmit the energy from the tool 27 to the foot piece 58 and which is capable of being destroyed when the foot piece 58 is sufficiently warmed by the energy.

For the implantation, the implant as shown in FIG. 11 is held and guided into the opening provided for its implantation with the aid of the implantation tool 27 and is held in place by a counter element 59. The implantation tool 27 is then e.g. vibrated and simultaneously pulled in a direction away from the implant. Through the vibrational energy, the liquefiable material of the distal end of the tubes 57 and possibly of the proximal face of the foot pieces 58 is liquefied and penetrates into the bone tissue. Therewith the tubes 57 get shorter and are eventually welded to the foot pieces 58. As soon as a sufficient amount of the liquefiable material is liquefied and the foot pieces 58 are warm enough, the pulling force on the vibration tool 27 is increased for separating the distal tool ends from the foot pieces 58, which remain anchored in the bone tissue to constitute distal ends of the anchoring pins 1 as shown on the right hand side of FIG. 11.

A similar implantation result can be achieved by using, instead of vibrational energy, electromagnetic radiation which is coupled e.g. through the counter element 59 into the polymer tube 57 or through an implantation tool of the same form as the illustrated tool 27 into the foot piece 58 to be absorbed in a distal part of the polymer tube 57 or in the foot pieces 58 of the tool, in the same manner as described for the implant as illustrated in FIGS. 8A to 8C and 9.

Figure 12:
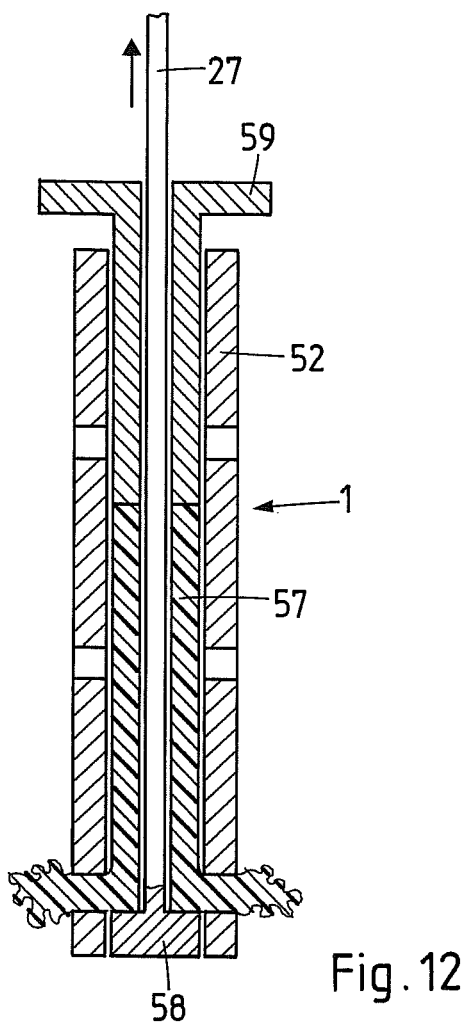
FIG. 12 is a sectional elevation view of a further exemplary embodiment of a one-part implant similar to the implants of FIGS. 1 and 8A to 8C.

FIG. 12 shows an anchoring pin 1 of a further exemplary embodiment of the implant according to the invention as well as a distal end portion of an implantation (preferably vibration) tool 27 suitable for implantation of the implant. The implant may have a similar form as the implant according to FIGS. 8A to 9C. The anchoring pin 1 of the implant is designed for being anchored in the bone tissue using the anchoring technique as described in the publication WO 2009/132472, the content of which is enclosed herein by reference. This anchoring technique is a combination of the anchoring techniques as shortly described in connection with FIGS. 10 and 11. For this reason, the anchoring pin 1 comprises a perforated sheath 52 and the liquefiable material is provided inside the sheath 52 in the form of a polymer tube 57 through which the distal end of the implantation tool 27 reaches, carrying a distal foot piece 58 beyond the polymer tube 57. The polymer tube 57 is held in place inside the sheath 52 with a counter element 59. For anchoring it in bone tissue, the anchoring pin 1 as shown in FIG. 12 is positioned in a corresponding bore, the polymer tube being held in place with a counter element 59. Then, the implantation tool 27 is e.g. vibrated and is pulled in a direction away from the bone tissue, such that the polymer material is liquefied between the distal face of the polymer tube 57 and the proximal face of the foot piece 58 and is pressed through the sheath perforations to penetrate into the bone tissue outside the sheath 52. Therein it is possible to equip the sheath with perforations at a plurality of distinct depths and to liquefy polymer material in these distinct depth in distinct liquefaction steps between which the foot piece is moved from one such depth to a next higher one, the vibration being switched off. After a last liquefaction step the counter element 58 and the implantation tool 27 are removed from the sheath 52, wherein a rest of the polymer tube 57 and the foot piece 58 remain in the sheath 52 (similar to the anchoring process as described in connection with FIG. 11) or are removed from the sheath. In the latter case the foot piece 58 may, as illustrated, be made of a non-liquefiable material.

In the same manner as described further above for the implants as illustrated in FIGS. 8A to 8C, and 9 to 11, implantation of the implant comprising anchoring pins as illustrated in FIG. 12 is possible also with the aid of radiation energy (preferably laser light of the visible or infrared frequency range) or rotational energy instead of the above described vibrational energy. For the latter case, an implantation tool of the same form as the above described vibration tool 27 is used and is connected to a rotation drive, while the counter element 59 is equipped for not only holding the polymer tube 57 against the foot piece 58 but also for preventing the polymer tube from rotating together with the tool. Friction heat created between the distal face of the non-rotating polymer tube 57 and the proximal face of the rotating foot piece 58 liquefies the distal end of the polymer tube and makes the liquefied material pass through the perforations of the sheath 52. Furthermore, liquefaction can be achieved by coupling electromagnetic radiation e.g. into the counter element 59 and from there into the polymer tube 57 to be absorbed in the polymer tube 57 or in the foot piece 58. A further way for creating the thermal energy needed for the liquefaction consists in electrically heating the proximal face of the foot piece 58.

FIG. 13 shows a further embodiment of the implant according to the invention which implant, when implanted, resembles the implant according to FIG. 8A to 8C or 9 but before implantation comprises the anchoring pins 1 and the bridge portion 2 as separate parts (three-part implant or possibly multi-part implant). The bridge portion 2 is designed for being introduced into the opening provided for it and for being then fixed by introducing the anchoring pins 1 (preferably simple polymer pins) through bores 55 in the bridge portion 2 and anchoring them then in the bone tissue underneath the bridge portion. The bridge portion 2 is preferably substantially wedge shaped and comprises two (or more than two) through bores 55 extending from the proximal face 4 to a distal face and preferably having a diameter which is smaller than the thickness of the bridge portion 2 at the proximal face 4 and larger than the thickness of the bridge portion 2 at the distal face such that the distal bore mouths extend from the distal face onto the lateral surfaces of the bridge portion 2 towards the proximal face.

FIG. 13 shows on the left hand side the anchoring pins 1 before being introduced in the bores 55 of the bridge portion 2, i.e. it shows the implant before implantation, and on the right hand side a section through the implant after implantation. For the anchoring pins 1 being able to fix the bridge portion 2 firmly in the opening, it is advantageous to provide in the bores 55 of the bridge portion 2 a further liquefiable material which is welded to the liquefiable material of the anchoring pins on implantation, or a surface structure, into which the liquefiable material of the anchoring pins is pressed on implantation. A similar effect can be achieved by equipping the anchoring pins 1 with heads, or, as illustrated, to form such heads 56 by applying further e.g. vibrational energy for plasticizing and correspondingly deforming the material of the proximal end of the anchoring pins 1.

For providing the bores in the bone tissue for accommodating the distal ends of the anchoring pins it is possible to use a drill guide as shown in FIG. 5C or to use the positioned bridge portion 2 of the implant as drill guide.

As already described for the implant as illustrated in FIGS. 8A to 8C and 9, it is possible for the implant according to FIG. 13 to use for the implantation or the liquefaction of the liquefiable material respectively, instead of vibrational energy, electromagnetic radiation and to provide means for absorbing such radiation in or adjacent to the location in which such liquefaction is desired. For such purpose, the bridge portion 1 comprises an absorbing agent or the radiation is absorbed by the bridge portion 2.

Instead of the anchoring pins as illustrated in FIG. 13 to be anchored in bores and possibly welded into the bridge portion with the aid of a liquefiable material and e.g. vibrational energy, it is possible also to use anchoring pins as illustrated in FIGS. 10 to 12.

FIG. 14 illustrates an exemplary application of an implant similar to the implant according to FIG. 13. The bridge portion 2 of this implant has the form of a part circle and is suitable for stabilizing a part circular cut 13 e.g. produced in the tibial plateau leveling osteotomy illustrated in FIG. 2. The procedure of implanting the implant into the circular cut may be the same as described before for the implant according to FIG. 13. Following an alternative procedure, the anchoring pins 2 are anchored in corresponding bores first and then the bridge portion is positioned on the proximal heads of the anchoring pins and the heads (not shown) of the anchoring pins are then formed. The bores for accommodating the anchoring pins are drilled using a separate drill guide or the bridge portion.

In the implant according to FIG. 14 to be implanted as above described it is advantageous to provide openings 55, which are not exactly adapted to the cross section of the anchoring pins but are e.g. slot-shaped. The proximal ends of the anchoring pins will adapt to the shape of the openings during the head forming. Furthermore it may be advantageous not to provide a groove along the cut but to position the bridge portion on the bone surface. For further stabilization of the bridge portion, the latter may comprise a plurality of small thorns (not shown) along its lateral edges, which thorns are impacted in the bone surface on positioning the bridge portion 2.

Figure 15A:
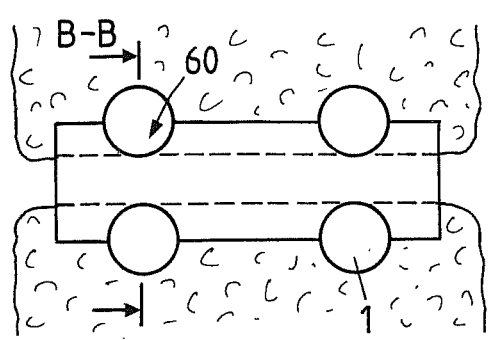
FIG. 15A is a plan view that shows a further embodiment of the implant according to the invention, which is based on the same principle as the implant according to FIG. 13.
Figure 15B:
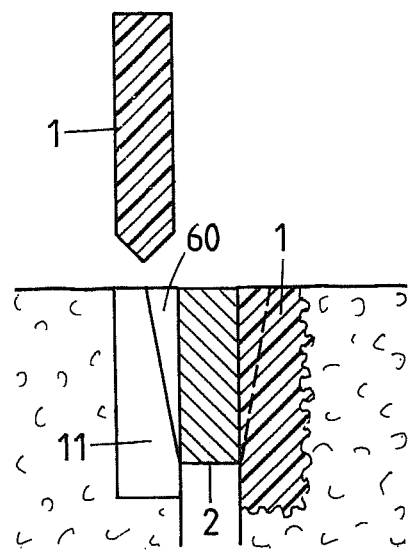
FIG. 15B is a sectional elevation view that shows a further embodiment of the implant according to the invention, which is based on the same principle as the implant according to FIG. 13.

FIGS. 15A and 15B show a further embodiment of the three-part or multi-part implant according to the invention, the embodiment being based on the same principle as the implant according to FIG. 13. The implant is illustrated in FIG. 15A viewed from the side of the proximal face and after implantation, and in FIG. 15B in section (section plane designated with B-B in FIG. 15A) and in a partly implanted state. The implant comprises a bridge portion 2 and four anchoring pins 1, wherein the bridge portion 2 has e.g. the form of a wedge and comprises two grooves 60 on either side for receiving the anchoring pins 1.

In contrast to the implant illustrated in FIG. 13, the anchoring pins 1 of the implant according to FIGS. 15A and 15B does not extend through openings in the bridge portion 2 but are positioned on both sides of the bridge portion, wherein a bore (or opening with another than circular cross section) adapted to receive one of the anchoring pins is preferably situated partly in the bridge portion (groove 60) and partly in the bone tissue.

As for the implant according to FIG. 13, the implant according to FIGS. 15A and 15B are implanted by firstly pushing the bridge portion into the opening and by then positioning the anchoring pins and anchoring them in the bone tissue. Therein the bores in the bone tissue for accommodation of the anchoring pins may be drilled before positioning the bridge portion 2 using a drill guide e.g. as illustrated in FIG. 5C or they may be drilled after positioning the bridge portion 2, using the latter as a drill guide.

Before implantation of the implant according to FIG. 13, a groove is provided for the bridge portion 2, wherein a depth of the groove is the same or larger than the depth of the bridge portion, such that on positioning the bridge portion 2, its proximal face is flush with the bone surface. In a preferred application of the implant according to FIGS. 15A and 15B, the bridge portion 2 is made of a bone replacement material such as e.g. calcium phosphate, hydroxyapatite, allograft bone tissue or a preparation made of allograft bone tissue, and the implant is used for stabilizing bone portions comprising bone tissue of a reduced mechanical stability.

The anchoring pins 1 of the implant according to FIGS. 15A to 15B are again anchored in the bone tissue with the aid of a liquefiable material, wherein the liquefiable material is arranged on the anchoring pins in any of the ways as discussed further above. Therein it is advantageous to simultaneously with the anchoring in the bone tissue to connect the anchoring pins with the bridge portion, e.g. by providing a suitably structured surface on the bridge portion where the anchoring pins are to be attached and by providing the liquefiable material on both sides of the anchoring pins, on one side for establishing a positive fit connection with the bone tissue and on the other side for establishing a positive fit connection with the surface structure of the bridge portion 2. Further examples of methods for in situ attaching implant parts to each other and simultaneously anchoring them in bone tissue are described in the publication WO 2008/034276 which is incorporated herein in its entirety by reference.

FIGS. 16 to 19 show further exemplary embodiments of the implant according to the invention, the implants comprising numbers of anchoring pins and/or bridge portions which are different form such numbers of the embodiment according to FIGS. 8A to 8C. Virtually all above comments regarding the implant, in particular the various designs of the anchoring pins as shown in FIGS. 9 to 12, the corresponding anchoring techniques, and the design of multi-part devices as illustrated in FIGS. 13 and 15A/B are adaptable to these further embodiments of the implant in a straightforward manner.

The implant according to FIG. 16 comprises one only anchoring pin 1 and a bridge portion 2 reaching laterally beyond the anchoring pin. The implant according to FIG. 17 comprises two anchoring pins 1 and a two-part bridge portion 2 therebetween. The implant according to FIG. 18 comprises two anchoring portions 1 and a bridge portion 2 reaching laterally beyond the two anchoring pins 1 and comprising through openings. The implant according to FIG. 19 comprises two anchoring pins 1 and a bridge portion 2 joined to the anchoring portion 1 in a central region between the distal and proximal ends thereof. All implant embodiments according to FIGS. 16 to 19 may comprise more than two anchoring pins 1 and a corresponding number of bridge portions 2.

What is claimed is:

1. A set of tools for stabilizing two bone portions separated by a cut or fracture in a human or animal patient, the set of tools comprising an implantation tool and mounted or mountable to the implantation tool an implant, wherein the implant comprises a plurality of anchoring pins and at least one bridge portion connecting proximal ends of the anchoring pins and wherein a material having thermoplastic properties is arranged on lateral surfaces of the anchoring pins or in a perforated sheath of at least one anchoring pin, wherein said lateral surfaces of the anchoring pins or said perforated sheath is arranged on the implant for being in contact with bone tissue on implantation, wherein the set of tools further comprises a fixation/guide tool comprising an axial tunnel and resilient outwards flaring distal half portions with distal faces equipped for fixation on a bone surface, wherein the distal half portions flare outwards with respect to a longitudinal axis of the fixation/guide tool.

2. The set of tools according to claim 1 and further comprising means for forcing the distal half portions against each other and locking the distal half portions in a position.

3. The set of tools according to claim 1 and further comprising at least one of a cut finder, a drill guide and a corresponding drill, a cutter guide and a corresponding cutter, the cut finder, the drill guide and the cutter guide having cross sections adapted to a cross section of the axial tunnel of the fixation/guide tool such that the cut finder, the drill guide and the cutter guide can be introduced into the axial tunnel.

* * * * *